United States Patent [19]

Duffett

[11] Patent Number: Plant 5,660

[45] Date of Patent: Feb. 11, 1986

[54] CHRYSANTHEMUM PLANT NAMED CHIC

[75] Inventor: William E. Duffett, Salinas, Calif.

[73] Assignee: Yoder Brothers, Inc., Barberton, Ohio

[21] Appl. No.: 574,706

[22] Filed: Jan. 27, 1984

[51] Int. Cl.[4] ..... A01H 5/00

[52] U.S. Cl. ..... Plt./74

[58] Field of Search ..... Plt./74

*Primary Examiner*—Robert E. Bagwill

*Attorney, Agent, or Firm*—Schwartz, Jeffery, Schwaab, Mack, Blumenthal & Evans

[57] ABSTRACT

A chrysanthemum plant known by the cultivar name Chic and particularly characterized as to uniqueness by the combined characteristics of flat capitulum form; daisy capitulum type; purple ray floret color; diameter across face of capitulum ranging from 5 to 7 cm. at maturity; uniform eight week flowering response; medium plant height; upright branching pattern; tolerance of low winter 13° C. minimum temperatures; and tolerance of high summer temperatures of 24° C. nights, and 38° C. days under high light environments.

3 Drawing Figures

The present invention comprises a new and distinct cultivar of *Chrysanthemum morifolium,* Ramat. named Chic.

Chic is a product of a planned breeding program which had the objective of creating new chrysanthemum cultivars for pinched spray pot mum programs having daisy capitulum type, purple floret color, eight week flowering response and the ability to produce commercially acceptable quality in year round programs. Such traits in combination were not present or required improvement in previously available commercial cultivars.

Chic was originated from a cross made in a controlled breeding program in Salinas, Calif. in 1980. The female parent was an unnamed seedling identified as 79121007, originated by the present inventor from a hybridization of unnamed seedling 76025024 and Circus, disclosed in U.S. Plant Pat. No. 4,188. The male parent of Chic was an unnamed seedling identified as 79121001, originated from the same cross.

Chic was discovered and selected as one flowering plant within the progeny of the stated cross by William E. Duffett on July 31, 1981 in a controlled environment in Salinas, Calif.

The first act of asexual reproduction of Chic was accomplished when vegetative cuttings were taken from the initial selection in October 1981 in a controlled environment in Salinas, Calif. by a technician working under formulations established and supervised by William E. Duffett. Horticultural examination of selected units initiated February 1982 has demonstrated that the combination of characteristics as herein disclosed for Chic are firmly fixed and are retained through successive generations of asexual reproduction.

Chic has not been observed under all possible environmental conditions. The phenotype may vary significantly with variations in environment such as temperature, light tensity and day length. The observations, measurements and comparisons describe plants grown in Salinas, Calif. and Leamington, Ontario, Canada under greenhouse conditions which approximate those generally used in commercial practice.

The following traits have been repeatedly observed and are determined to be basic characteristics of Chic which in combination distinguish this chrysanthemum as a new and distinct cultivar:

(1) Flat capitulum form.

(2) Daisy capitulum type.

(3) Purple ray floret color.

(4) Diameter across face of capitulum ranging from 5 to 7 cm. at maturity.

(5) Uniform eight week photoperiodic flowering response to short days.

(6) Medium plant height (requiring 2 long day weeks prior to pinch and short days, and 1 to 2 applications of 2500 ppm B-9 SP, the first at 14, the second at 21 days after the beginning of short days to attain a flowered plant height of 25 to 35 cm. in 6" pots).

(7) Upright branching pattern.

(8) Low temperature tolerance of 13° C. minimum.

(9) High temperature tolerance of 24° C. nights and 38° C. days under high light environments.

The accompanying photographic drawings depict typical leaf and inflorescence characteristics of Chic. Sheet 1 is a color photograph of two plants of Chic grown as pinched spray pot mums, with colors being as accurate as possible with renditions of this type. The plant on the left depicts true flower color (immature) at prime marketable stage, and the plant on the right illustrates mature flower color one week later. Sheet 2 is a black and white photograph of three views of the inflorescence of Chic. Sheet 3 shows the leaves of Chic in three stages of growth (mature, intermediate and immature).

Of the many commercial cultivars known to the present inventor, the most similar in comparison to Chic is Circus. Reference is made to attached Chart A which compares certain characteristics of Chic to those same characteristics of Circus.

Similar traits are the plant height, capitulum form, type and diameter. Chic has deeper ray floret color, more upright branching pattern, faster response time, and superior tolerance of both high and low temperatures for bud initiation and development. Both Chic and Circus have abundant pollen. Chic has a smaller diameter of disc.

In the following description, color references are made to The Royal Horticultural Society Colour Chart. The color values were determined between 10:00 A.M. and 10:15 A.M. on Dec. 1, 1983 under 150 foot-candle light intensity at Salinas, Calif.

Classification:

*Botanical.*—*Chrysanthemum morifolium,* Ramat. cv Chic.

*Commercial.*—Daisy spray pot mum.

I. Inflorescence:

A. *Capitulum.*—Form: Flat. Type: Daisy. Diameter across face: 5 to 7 cm.

B. *Corolla of ray florets.*—Color (General Tonality From a Distance of Three Meters): Red-Purple. Color (upper surface): 61A (immature) to 64 A,B (mature): 61A and 64A-B. Color (under surface): 72B-C.

C. *Corolla of disc florets.*—Color (mature): 5 B-C including pollen. Color (immature): 144B-C. Shape: Oblong. Rounded tip.

C. *Corolla of disc florets.*—Color (mature): 5 B-C including pollen. Color (immature): 144B-C.

D. *Reproductive organs.*—Androecium: Present disc florets only; abundant pollen. Gynoecium: Present both ray and disc florets.

II. Plant:

A. *General appearance.*—Height: Medium. Branching Pattern: Upright.

B. *Foliage.*—Color (abaxial): 147A. Color (adaxial): 147B. Shape: Moderately lobed. Deeply serrated.

CHART A

COMPARISON OF CHIC AND CIRCUS

| CULTIVAR | RAY FLORET COLOR | CAPITULUM FORM AND TYPE | BRANCHING PATTERN |
|---|---|---|---|
| CHIC | PURPLE | FLAT DAISY | UPRIGHT |

CHART A-continued

COMPARISON OF CHIC AND CIRCUS

| CIRCUS | LAVENDER | FLAT DAISY | SEMI SPREADING |
|---|---|---|---|
| CULTIVAR | DIAMETER ACROSS FACE OF CAPITULUM | PLANT HEIGHT | FLOWERING RESPONSE PERIOD | TEMPERATURE TOLERANCE |
| CHIC | 5 to 7 cm. | MEDIUM 30 to 35 cm. | 8 WEEK | 13° C. - UNIFORM 24°, 38° C. - UNIFORM |
| CIRCUS | 5 to 7 cm. | MEDIUM 30 to 45 cm. | 9 WEEK | 13° C. - UNEVEN 24°, 38° C. - SLOW, COLOR DULLS |

COMPARISONS MADE OF PLANTS GROWN AS A PINCHED SPRAY POT MUM IN SALINAS, CALIFORNIA AND LEAMINGTON, ONTARIO, CANADA

I claim:

1. A new and distinct cultivar of *Chrysanthemum morifolium,* Ramat., plant named Chic, as described and illustrated, and particularly characterized as to uniqueness by the combined characteristics of flat capitulum form; daisy capitulum type; purple ray floret color; diameter across face of capitulum ranging from 5 to 7 cm. at maturity; uniform eight week flowering response; medium plant height; upright branching pattern; tolerance of low winter 13° C. minimum temperatures; and tolerances of high summer temperatures of 24° C. nights, and 38° C. days under high light environments.

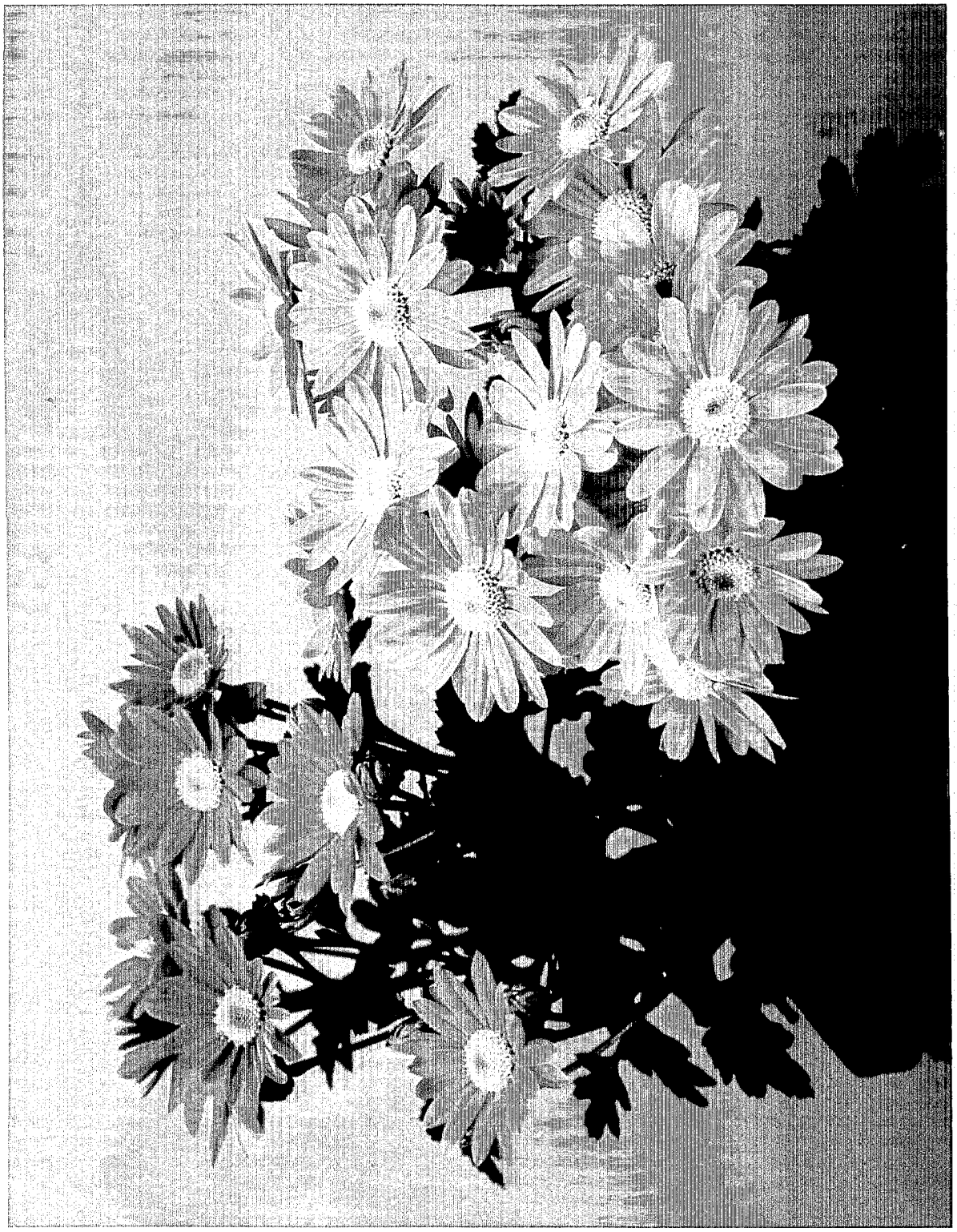

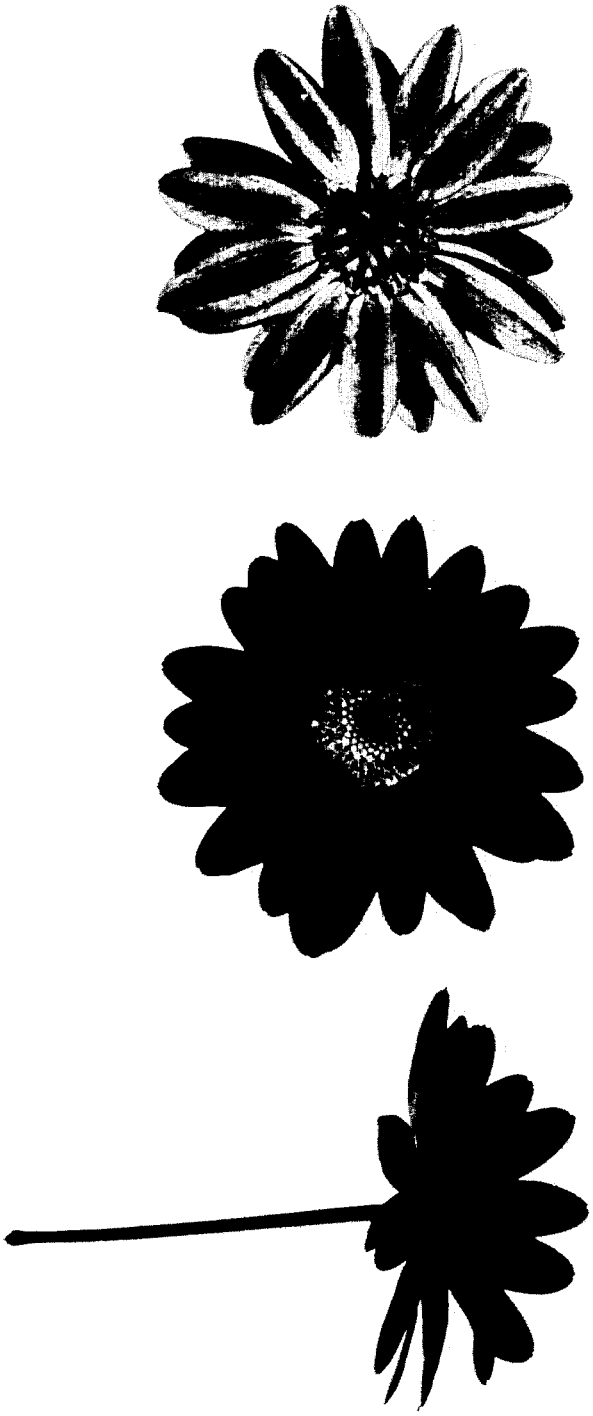

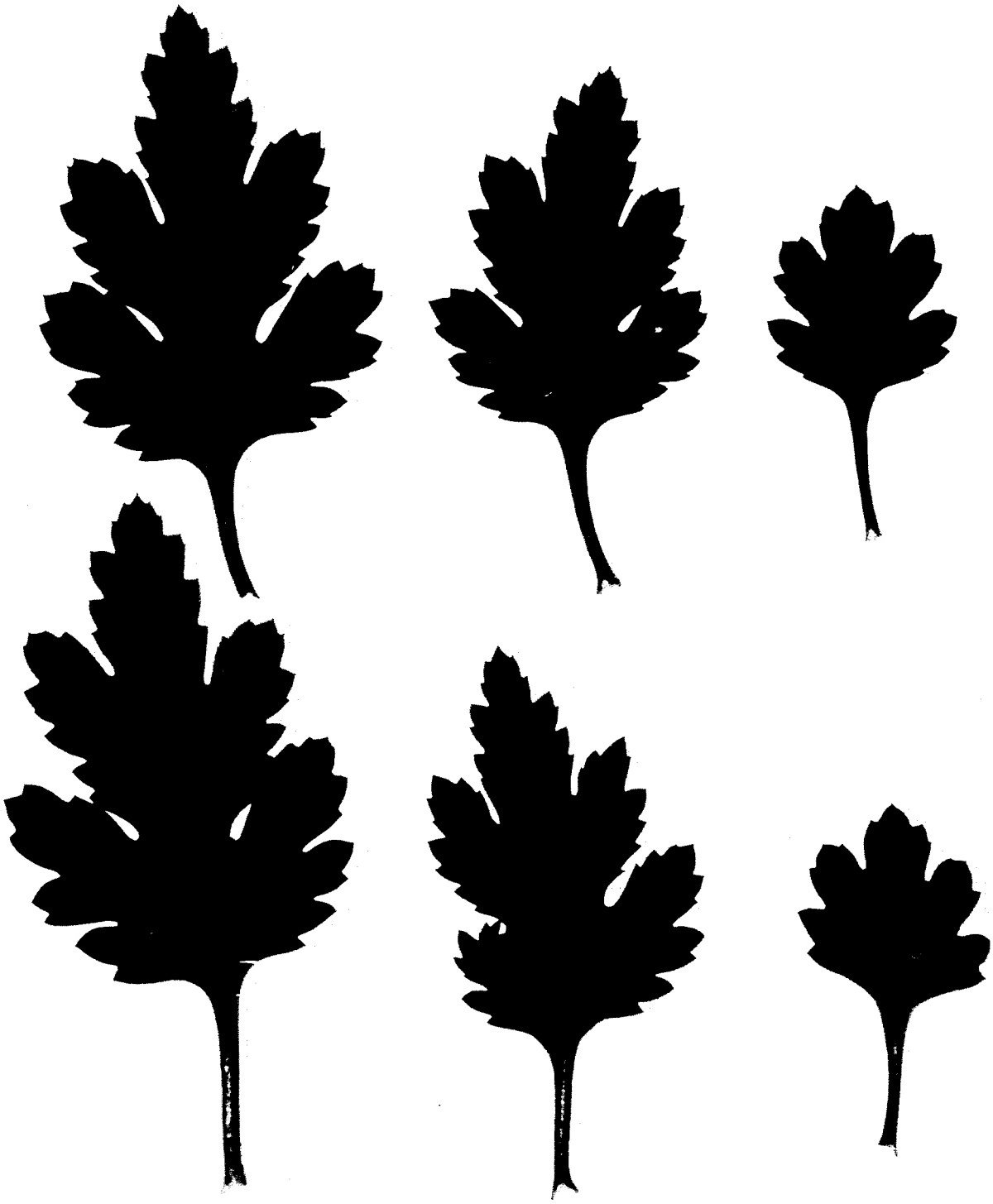

* * * * *